(12) United States Patent
Ischinger

(10) Patent No.: US 6,682,556 B1
(45) Date of Patent: Jan. 27, 2004

(54) APPLICATION CATHETER AND METHOD OF IMPLANTATION OF A STENT IN VASCULAR BIFURCATIONS, SIDE BRANCHES AND OSTIAL LESIONS

(75) Inventor: Thomas Ischinger, München (DE)

(73) Assignee: Vascular Concepts Holdings Limited (GB)

( * ) Notice: Subject to any disclaimer, the term of this patent is extended or adjusted under 35 U.S.C. 154(b) by 0 days.

(21) Appl. No.: 09/462,953
(22) PCT Filed: Jul. 17, 1998
(86) PCT No.: PCT/IB98/01296
§ 371 (c)(1), (2), (4) Date: Jan. 14, 2000
(87) PCT Pub. No.: WO99/03426
PCT Pub. Date: Jan. 28, 1999

(30) Foreign Application Priority Data

Jul. 18, 1997 (EP) .............................................. 97112382

(51) Int. Cl.[7] .................................................. A61F 2/06
(52) U.S. Cl. ........................ 623/1.35; 623/1.1; 606/194; 604/103.04
(58) Field of Search ............ 604/96.01, 102.01–102.03, 604/103.04–103.09; 606/108, 192, 191, 194, 195, 198; 623/1.1, 1.11, 1.15, 1.23, 1.37, 1.16, 1.22; 600/433–435

(56) References Cited

U.S. PATENT DOCUMENTS

| | | | |
|---|---|---|---|
| 4,983,167 A | | 1/1991 | Sahota |
| 5,137,513 A | * | 8/1992 | McInnes et al. ........ 604/103.05 |
| 5,263,932 A | | 11/1993 | Jang |
| 5,324,269 A | * | 6/1994 | Miraki ....................... 604/160 |
| 5,749,825 A | * | 5/1998 | Fischell et al. ................ 600/3 |
| 5,800,520 A | * | 9/1998 | Fogarty et al. ............. 606/194 |
| 6,007,517 A | * | 12/1999 | Anderson .............. 604/103.04 |
| 6,048,361 A | | 4/2000 | Von Oepen |
| 6,270,465 B1 | * | 8/2001 | Keith et al. ................. 600/585 |

FOREIGN PATENT DOCUMENTS

| | | |
|---|---|---|
| WO | WO 96/34580 | 11/1996 |
| WO | WO 96/36269 | 11/1996 |
| WO | WO 96/41592 | 12/1996 |

* cited by examiner

Primary Examiner—LoAn H. Thanh
(74) Attorney, Agent, or Firm—Fleit, Kain, Gibbons, Gutman, Bongini & Bianco; Paul D. Bianco; Martin Fleit

(57) ABSTRACT

A dilatation catheter is disclosed having an inflation balloon and a catheter shaft with an inflation channel. A first guidewire channel is disposed along the dilatation catheter and has a distal exit at the distal end of the catheter shaft. A second guidewire channel is disposed along the dilatation catheter and has a distal exit attached along the inflation balloon. Guidewires are slideably disposed within the first and second guidewire channels. An oblique ended expandable stent is disposed about the inflation balloon and used to treat bifurcated and sidebranched arteries and ostial lesions.

5 Claims, 6 Drawing Sheets

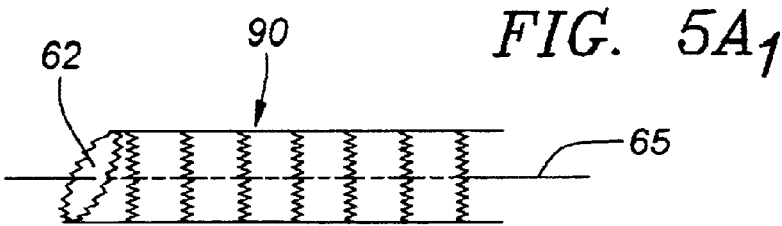
FIG. 5A₁
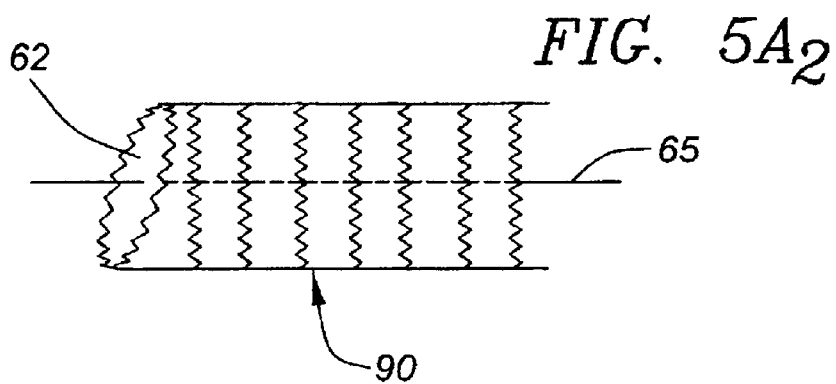
FIG. 5A₂
FIG. 5B₁
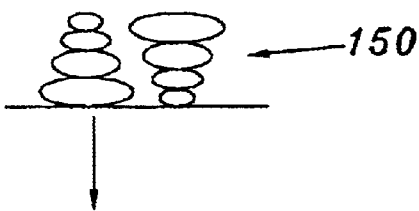
FIG. 5C₁
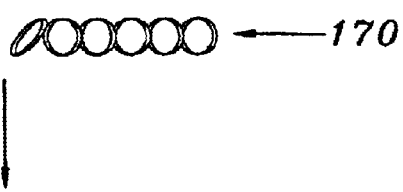
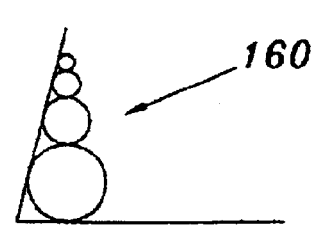
FIG. 5B₂
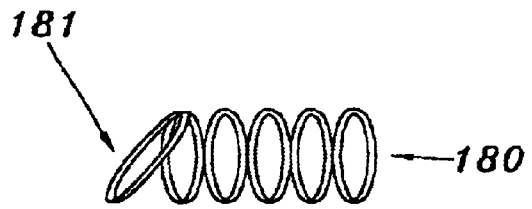
FIG. 5C₂

APPLICATION CATHETER AND METHOD OF IMPLANTATION OF A STENT IN VASCULAR BIFURCATIONS, SIDE BRANCHES AND OSTIAL LESIONS

TECHNICAL FIELD

This invention relates to a stent and its implantation into blood vessels. More particular, it relates to a stent and an application catheter used to implant the stent into vascular bifurcations, side branches and ostial lesions.

BACKGROUND ART

Stents are prostheses to support the lumen of hollow organs, primarily to acutely maintain the lumen of blood vessels after mechanical interventions such as balloon angioplasty and to achieve a better long term result after such mechanical interventions. While implantation of stents into straight vessel segments poses little technical problems, implantation of stents into ostial lesions, sidebranches or into vessel bifurcations represents a challenge to the operator and carries increased risks of acute and long-term failure, in particular due to misplacement or imprecise placement.

In ostial lesions, the proximal end of the stent must be precisely placed at the ostium of the artery so that the stent is not protruding into the aortic lumen. In order to avoid the above risk, the stent is sometimes advanced too far into the artery causing the initial segment of the diseased ostium to remain unstented.

A similar problem exists with stenting of sidebranches and vessel bifurcations. For both situations, precision placement techniques are required for optimal results. However, the operator must rely on visual assessment during fluoroscopy with and without contrast injections. Contrast injections are of little help for stenting in ostial lesions, since opacification of the target artery is usually inadequate and identification of the aortic lumen and the ostial takeoff is very limited. In sidebranch and bifurcational lesions, precise placement is similarly difficult due to poor identification of the exact beginning of the sidebranch ostium and the often non-perpendicular nature of the plane of the sidebranch in relation to the axis of the major vessel. The beating heart makes maintaining of a catheter position with current techniques even more difficult if not impossible.

The current invention offers a unique solution to the technical problems as described above.

SUMMARY OF THE INVENTION

A dilation catheter has a distal exit of a first guidewire channel located distally from an inflatable balloon portion and a distal exit of a second guidewire channel located proximally from the distal exit of the first guidewire channel. The distal exit of the second guidewire channel is located along the inflatable balloon portion or other expandable portion of the dilatation catheter. An oblique ended expandable stent is mounted therearound and used to treat bifurcated and sidebranched arteries and ostial lesions.

BRIEF DESCRIPTION OF DRAWINGS

FIG. 5A1 shows a sinusoidal ring configuration of a stent used in the present invention;

FIG. 5A2 shows a more detailed view of the FIG. 5A1;

FIG. 5B1 shows a non-expanded closed loop configuration used to form an oblique end of a stent in the present invention;

FIG. 5B2 shows an expanded closed loop configuration used to form an oblique end of a stent in the present invention;

FIG. 5C1 shows a non-expanded ratcheting band configuration used to form an oblique end of a stent in the present invention; and FIG. 5C2 shows an expanded ratcheting band configuration used to form an oblique end of a stent in the present invention.

DETAILED DESCRIPTION OF THE INVENTION

Figure 1A:
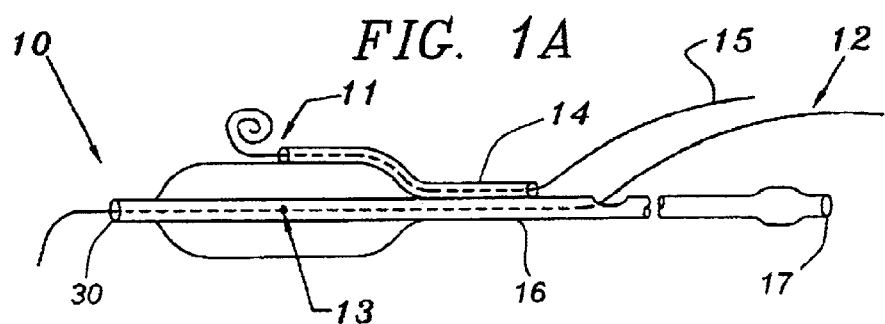
FIG. 1A shows a dilatation catheter of the present invention.

A balloon catheter as used for vascular dilatation commonly has a balloon inflation channel along the whole length of a pliable shaft of the balloon catheter up to the beginning or the mid-portion of the balloon, and a so called first guidewire channel 16 through which a first guidewire 12 is fed. The first guidewire channel 16 commonly exits at the distal end 10 of the balloon catheter (very distal catheter tip). Depending on whether the first guidewire channel 16 is running through the whole length of the balloon catheter shaft and exiting proximally at the proximal end 17 of the balloon catheter shaft or whether the first guidewire channel 16 is exiting via a side-exit 20 proximal to the balloon (i.e., the first guidewire channel 16 being substantially shorter than the whole catheter length), the balloon catheters are termed over the wire or monorail balloon catheters.

In order to create a technique to assist to mechanically self-position an application catheter, in an ostial, side branch or bifurcational lesion, or to orient the application catheter to a certain direction within a 360 degree circumference of the vessel, the application catheter must have a mechanical means to limit its advancement beyond a certain point and/or to direct the application catheter to the desired target. This is realized, as seen in FIGS. 1A–1D, by a distal exit 11 of a second guidewire channel 14 located along an inflatable portion of a balloon catheter (or other expandable means) used for stenosis dilatation (within the distal and proximal end of the balloon catheter) or along the respective portion used for stenosis dilatation or stent, drug or radiation application of any other application catheter or located within a short portion of length (i.e., 1–30 mm) beginning just proximal to the functional segment of a stent application catheter or other application catheter of other therapeutics and extending proximally.

The second guidewire channel 14 may run along the whole length of the balloon chatheter shaft, allowing the proximal exit of the second guidewire channel 14 to be located at the proximal end 17 of the balloon catheter shaft (over the wire fashion). Alternatively, the second guidewire channel 14 may be significantly shorter than the balloon catheter shaft, allowing the proximal exit of the second guidewire channel 14 to be located between the balloon inflation segment or the functional segment and the proximal end 17 of the balloon catheter shaft. A second guidewire 15 is threaded through the second guidewire channel 14. Preferably, but not necessarily, the proximal exit of the second guidewire channel 14 is within the distal half of the catheter so that easy monorail handling of the second guidewire channel 14 and second guidewire 15 is possible, as seen in FIG. 1A. In further reference to FIG. 1A, it is shown that the catheter has a distal end 10 through which a first guidewire 12 exits. A radiopaque marker 13 can be employed on the balloon catheter at the level of the distal exit 11 of the second guidewire channel 14. FIG. 1C illustrates the distal exit 30 of the first guidewire 12.

Figure 1B:
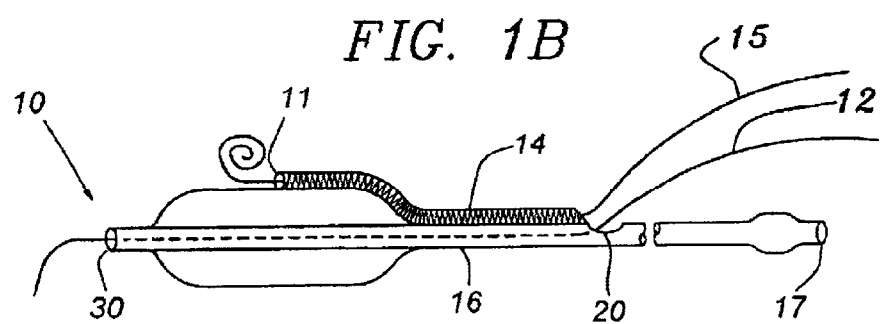
FIG. 1B shows an alternate embodiment of the catheter of the present invention.
Figure 1C:
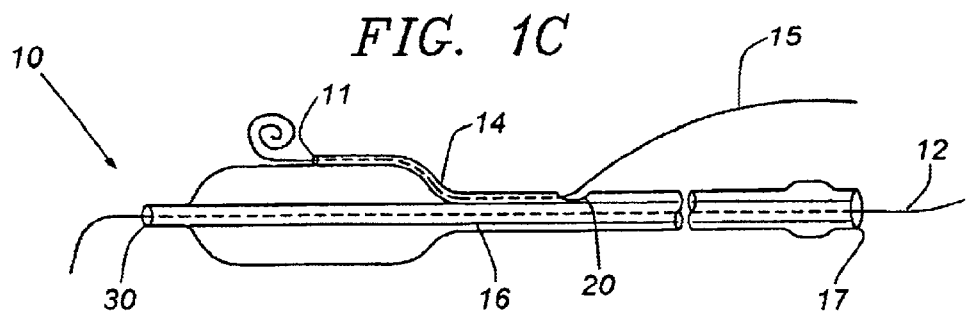
FIG. 1C shows another embodiment of the catheter of the present invention.
Figure 1D:
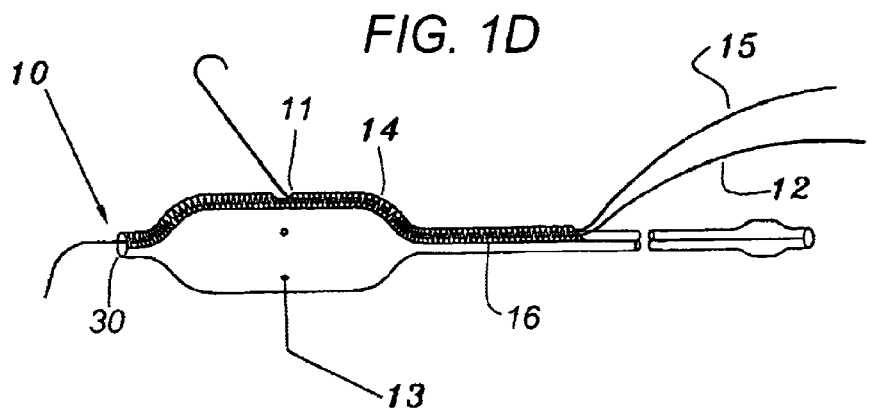
FIG. 1D shows another embodiment of the catheter of the present invention.
Figure 1E:
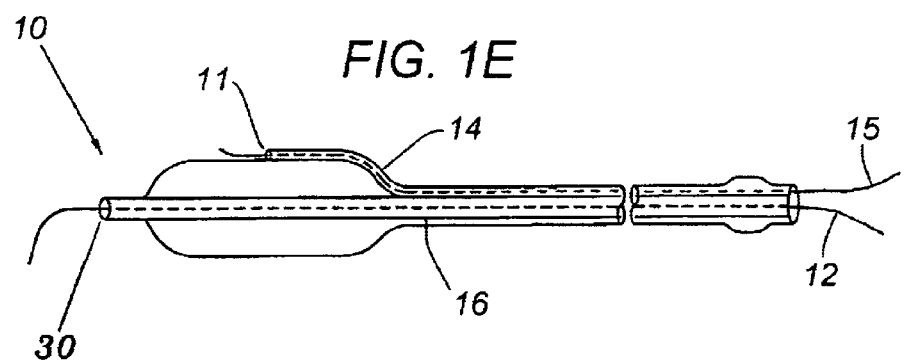
FIG. 1E shows still another alternate embodiment of the present invention having guidewire exits at the proximal end of the dilatation catheter.
Figure 1F:
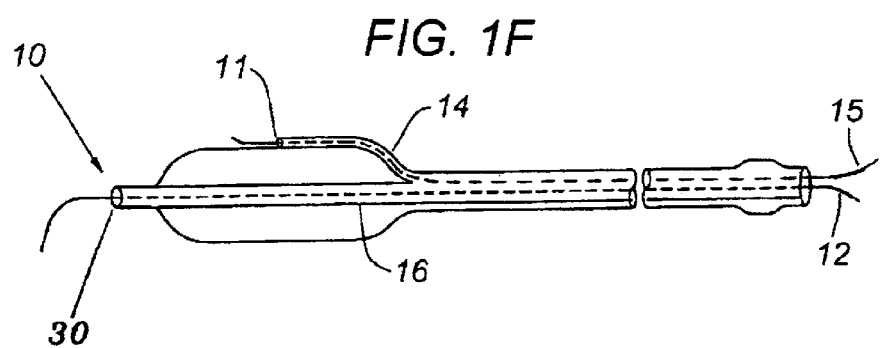
FIG. 1F shows yet another alternate embodiment of the present invention having two guidewire channels in fluid communication.

In an alternate embodiment, the second guidewire channel 14 merges with the first guidewire channel 16 over a certain distance or its total length and may use the same side exit 20 as the first guidewire channel 16, as seen in FIG. 1B, or the same exit at the proximal end 17 of the balloon catheter shaft (FIG. 1E).

In yet another alternate embodiment, as seen in FIG. 1D, the distal exit 11 of the second guidewire channel 14 is located on the first guidewire channel 16 intermediately positioned between the proximal end 17 of the catheter shaft and the distal end 10 of the catheter shaft; the first guidewire channel 16 is mounted to the outside of the balloon or other inflation means. Thus, the first guidewire channel 16 and the second guidewire channel 14 are the same channel over a certain segment.

To insert the stent of the present invention using a monorail type balloon catheter for bifurcational (or sidebranch) dilatation and stenting, the preferred steps include: placing the first guidewire 12 in the target artery (sidebranch); placing the second guidewire 15 in the main artery; advancing the balloon catheter over the first guidewire 12 (placed in the target lesion) which is threaded through the distal exit 30 of the first guidewire channel 16 at the distal end 10 of the balloon catheter and over the second guidewire 15 (main artery), which is threaded through the distal exit 11 of the second guidewire channel 14. The balloon is then advanced until the distal exit 11 of the second guidewire channel 14 reaches the bifurcation and prohibits any further advancement. However, an alternate sequence of steps is possible depending on the individual situation and types of catheter configuration used. It may be possible to partially or totally pre-load the second guidewire 15 into the second guidewire channel 14 and advance it through the distal exit 11 of the second guidewire channel 14 with the application catheter already inside the patient and/or coronary arteries. One or more radiopaque markers 13 make the location of the distal exit 11 of the second guidewire channel 14 visible to the operator.

This procedure permits stable positioning of a balloon catheter within a bifurcated vessel. But, more importantly, it orients the distal exit 11 of the second guidewire channel 14 automatically into the direction of the opening to the main artery, prohibiting any further rotation of the balloon, which may carry a stent or other therapeutic means. Thereby,.stents with oblique ends may be placed precisely into sidebranches.

Figure 4A:
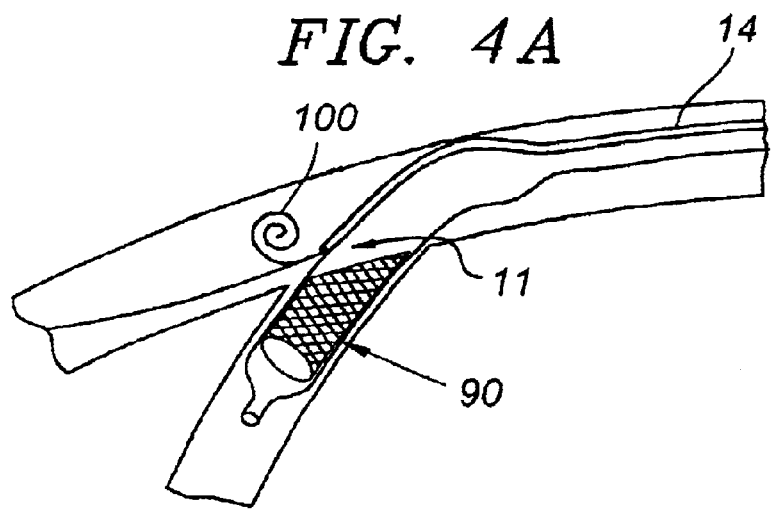
FIG. 4A shows the catheter of the present invention being used to insert an oblique ended stent into a bifurcated artery.
Figure 4B:
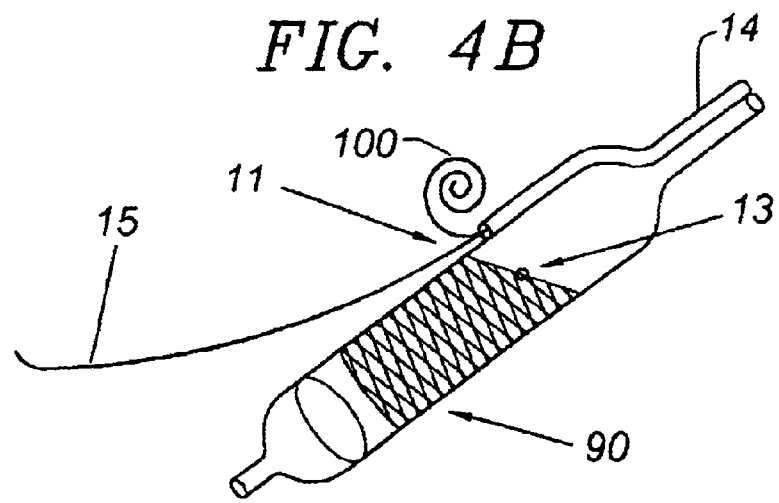
FIG. 4B shows the catheter of the present invention being used to insert an oblique ended stent, the catheter depicted outside an artery.
Figure 4C:
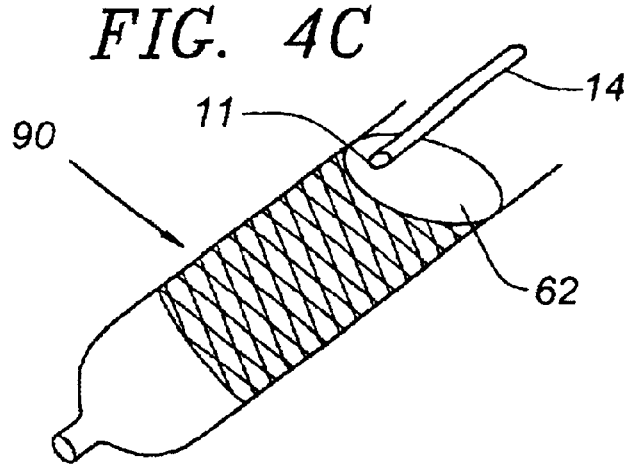
FIG. 4C is a top plan view, partially in section, of the configuration depicted in FIG. 4B showing the distal exit of the second guidewire channel located along the balloon catheter.

For stable balloon placement in ostial lesions, prepositioning of the second guidewire 15 is not necessary. In these cases, the second guidewire channel 14 may be pre-loaded and the second guidewire 15 may be advanced through the distal exit 11 of the second guidewire channel 14 once the balloon is approaching the target ostium. For ostial lesions, a plurality of guidewire channels 14 may be helpful and the guidewires used need no steerability but rather an atraumatic distal configuration and floppy property, e.g. mini-pigtail shape 100 (see FIG. 4A.), super-elasticity (e.g. use of the material Nitinol).

Figure 3A:
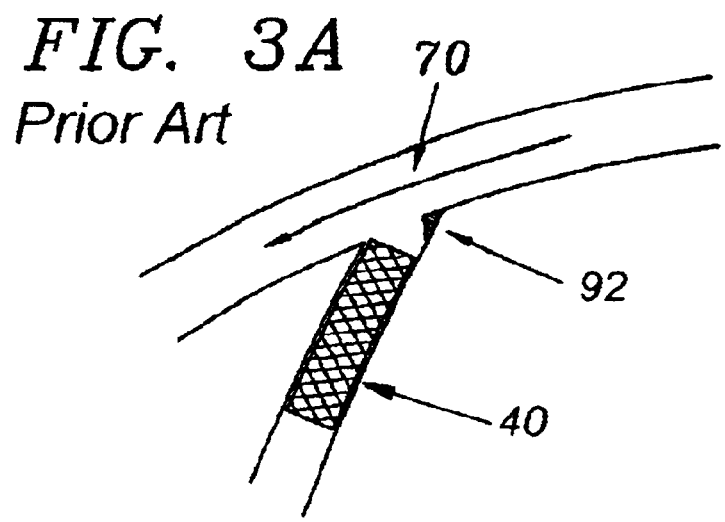
FIG. 3A illustrates prior art showing a non-oblique ended stent in a bifurcated artery having a lesion formed thereupon which is not covered by the non-oblique ended stent.
Figure 3B:
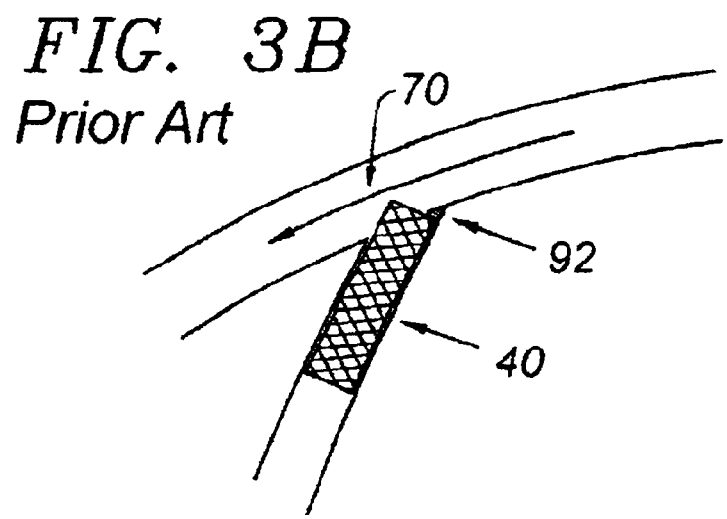
FIG. 3B illustrates prior art showing a non-oblique ended stent in a bifurcated artery having a lesion formed thereupon which is covered by the non-oblique ended stent but permits an end of the stent to protrude into the main artery.

The longitudinal axis of sidebranches are almost never perpendicular to the longitudinal axis of the vessel from which they are taking off. Therefore, the current stent 40 configurations of cylindrical tubular shape with the cross-sectional plane of the ends of the stent being perpendicular to the longitudinal axis of the cylinder stent 40 are inadequate. This configuration does not permit full stent coverage of the ostium of a sidebranch, as there is always the risk of protrusion of one edge of the end of the stent 40 into the lumen of the main artery 70, as shown in FIG. 3B. Stents with at least one oblique end are needed to better adapt to bifurcational anatomies, in particular the vessel takeoff angles.

Figure 2A:
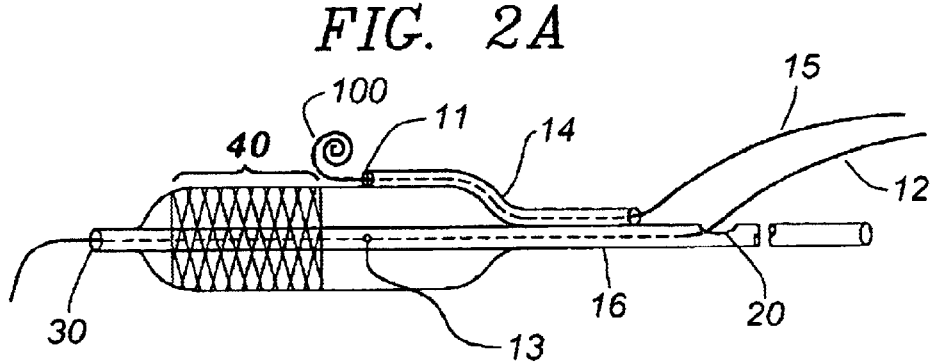
FIG. 2A shows the catheter of the present invention having a stent mounted therearound.
Figure 2B:
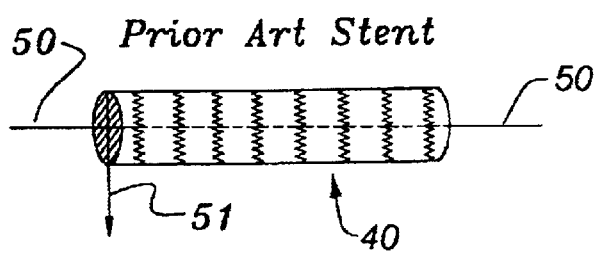
FIG. 2B shows a prior art stent having its end axis perpendicular to its longitudinal axis.
Figure 2C:
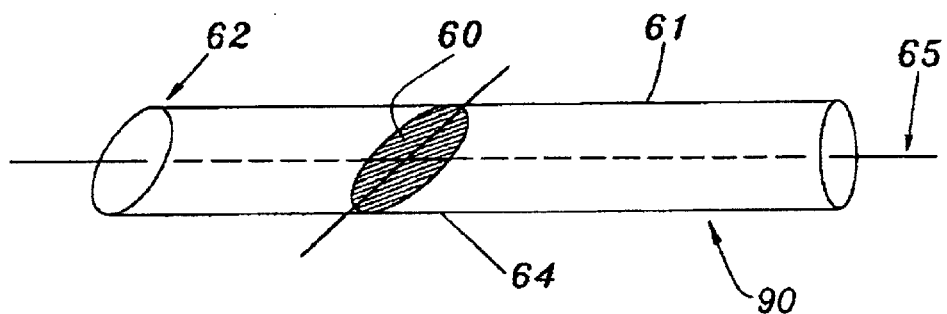
FIG. 2C shows an oblique ended stent used with the catheter of the present invention.

An oblique stent 90 is described, where one end of the stent cylinder is cut in a plane which is non perpendicular to the longitudinal axis of the stent, (i.e. oblique), preferentially in an angle of 80 to 45 degrees to the longitudinal axis of the stent (or 10 to 45 degrees to the axis perpendicular to the longitudinal axis of the stent), as seen in FIG. 2C. This configuration is defined by the short side 61 of the stent with a minimum length and the long side 64 of the stent with a maximum length. This configuration is further defined by a cross-sectional plane 60 representing the oblique stent end 62 which is non perpendicular to the longitudinal axis 65 of the stent. This is compared to a prior art stent 40 of FIG. 2B wherein the cross-sectional plane 51 of the stent end is perpendicular to the longitudinal axis 50 of the stent.

Figure 3C:
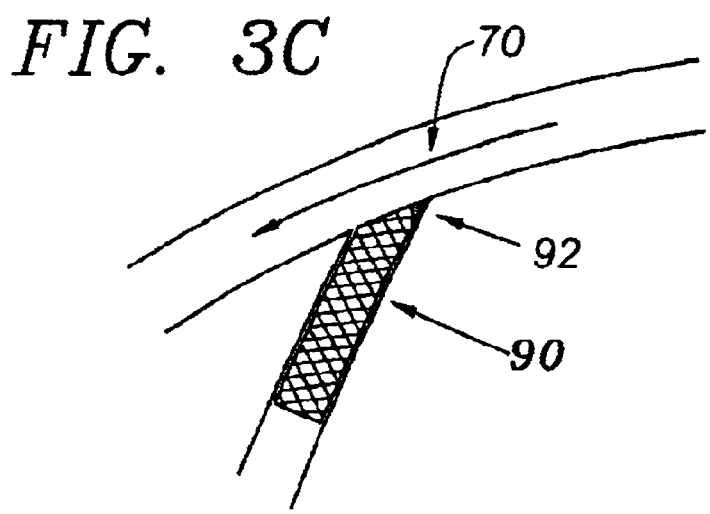
FIG. 3C shows an oblique ended stent used in the present invention which is capable of covering the lesion but prohibits an end portion of the stent from protruding into the main artery.

Placement and use of the oblique ended stent 90 is achieved if the stent carrying instrument, e.g. balloon catheter, can be directed so that the long and short sides, 64 and 61 respectively, of the stent are placed correctly in the ostium. This can be accomplished by the self-orienting catheter with a distal exit 11 of a second guidewire channel 14 of the present invention. The bifurcational stent will be mounted on the balloon such that the short side 61 of the stent 90 is closest to the distal exit 11 of the second guidewire channel 14. As seen in FIG. 3C, an oblique ended stent 90 of the present invention covers a lesion 92 and is placed properly in the bifurcated artery.

FIGS. 5A1 and 5A2 illustrate a sinusoidal ring configuration of a stent used in the present invention. The oblique end 62 of the stent 90 is non-perpendicular to the longitudinal axis 65 of the stent.

FIG. 5B1 illustrates a non-expanded closed loop configuration 150 used to form an oblique end of a stent in the present invention. FIG. 5B2 illustrates an expanded closed loop configuration 160 used to form the oblique end of the stent.

FIG. 5C1 illustrates a non-expanded ratcheting band configuration 170 used to form an oblique end of a stent in the present invention. FIG. 5C2 illustrates an expanded ratcheting band configuration 180 used to form the oblique end of the stent.

Equivalent elements and steps can be substituted for the elements and steps employed in this invention to obtain substantially the same results in substantially the same way.

What is claimed is:

1. The A dilatation catheter comprising:
   a shaft having proximal and distal ends;
   an inflatable balloon located at tile distal end of the shaft;
   an inflation channel in fluid communication with the inflatable balloon;
   a first guidewire channel having proximal and distal exits and extending along at least a portion of the shaft and configured and dimensioned to slideably receive a first guidewire; and
   a second guidewire channel having proximal and distal exits and being generally disposed on the shaft and configured and dimensioned to slideably receive a second guidewire, wherein the distal exit of the second guidewire channel is attached along the inflatable balloon and wherein the first and second guidewire channels are disposed on the inflation balloon.

2. The dilatation catheter of claim 1 wherein the distal exit of the first guidewire channel is generally located at the distal end of the shaft and the distal exit of the second guidewire channel is located along the inflation balloon.

3. The dilatation catheter of claim 2 wherein the first and second guidewire channels are in fluid connection with each other.

4. A dilatation catheter comprising:
   a shaft having proximal and distal ends;
   an inflatable balloon located at the distal end of the shaft;
   an inflation channel in fluid communication with the inflatable balloon;
   a first guidewire channel having proximal and distal exits and extending along at least a portion of the shaft and configured and dimensioned to slideably receive a first guidewire; and
   a second guidewire channel having proximal and distal exits and being generally disposed on the shaft and configured and dimensioned to slideably receive a second guidewire, wherein the distal exit of the second guidewire channel is attached along the inflatable balloon and wherein the proximal exits of the first and second guidewire channels are located at the proximal end of the shaft further wherein the first and second guidewire channels are in fluid connection with each other.

5. A dilation catheter comprising:
   a shaft having proximal and distal ends;
   an inflatable balloon located at the distal end of the shaft;
   an inflation channel in fluid communication with the inflatable balloon;
   a first guidewire channel having proximal and distal exits and extending along at least a portion of the shaft and configured and dimensioned to slideably receive a first guidewire; and
   a second guidewire channel having proximal and distal exits and being generally disposed on the shaft and configured and dimensioned to slideably receive a second guidewire, wherein:
   the distal exit of the second guidewire channel is attached along the inflatable balloon;
   a tubular expandable stent is disposed on a portion of the inflation balloon which is distal to the distal exit of the second guidewire channel, the stent having a distal end which is perpendicular to the longitudinal axis of the stent and a proximal end which is non-perpendicular to the longitudinal axis of the stent such that the stent has a short side and a long side; and
   the proximal end of the stent is positioned generally near the distal exit of the second guidewire channel and the short side of the stent is generally aligned with the distal exit of the second guidewire channel.

* * * * *

UNITED STATES PATENT AND TRADEMARK OFFICE
CERTIFICATE OF CORRECTION

PATENT NO. : 6,682,556 B1
DATED : January 27, 2004
INVENTOR(S) : Thomas Ischinger It is certified that error appears in the above-identified patent and that said Letters Patent is hereby corrected as shown below:

<u>Column 5,</u>
Line 26, delete "The"
Line 28, change "tile" to -- the --

Signed and Sealed this

Eighth Day of June, 2004

JON W. DUDAS
*Acting Director of the United States Patent and Trademark Office*